US012799546B2

(12) United States Patent
Uemori et al.

(10) Patent No.: US 12,799,546 B2
(45) Date of Patent: Nov. 17, 2026

(54) RNA VIRUS DETECTION METHOD

(71) Applicant: TAKARA BIO INC., Shiga (JP)

(72) Inventors: Takashi Uemori, Kusatsu (JP); Takehiro Sagara, Kusatsu (JP); Miwa Akitomo, Kusatsu (JP); Kensuke Saito, Kusatsu (JP)

(73) Assignee: TAKARA BIO INC., Shiga (JP)

( * ) Notice: Subject to any disclaimer, the term of this patent is extended or adjusted under 35 U.S.C. 154(b) by 941 days.

(21) Appl. No.: 17/921,451

(22) PCT Filed: Apr. 28, 2021

(86) PCT No.: PCT/JP2021/016998
§ 371 (c)(1),
(2) Date: Oct. 26, 2022

(87) PCT Pub. No.: WO2021/221109
PCT Pub. Date: Nov. 4, 2021

(65) Prior Publication Data

US 2023/0160023 A1 May 25, 2023

(30) Foreign Application Priority Data

Apr. 30, 2020 (JP) ................................ 2020-080247
Jun. 23, 2020 (JP) ................................ 2020-107940

(51) Int. Cl.
*C12Q 1/70* (2006.01)
*C12N 9/12* (2006.01)
*C12N 9/50* (2006.01)
*C12Q 1/6806* (2018.01)
*C12Q 1/6844* (2018.01)

(52) U.S. Cl.
CPC ............. *C12Q 1/70* (2013.01); *C12N 9/1252* (2013.01); *C12N 9/50* (2013.01); *C12Q 1/6806* (2013.01); *C12Q 1/6844* (2013.01); *C12N 2320/10* (2013.01)

(58) Field of Classification Search
CPC ....... C12Q 1/70; C12Q 1/6806; C12Q 1/6844
See application file for complete search history.

(56) References Cited

U.S. PATENT DOCUMENTS

| | | | |
|---|---|---|---|
| 8,642,266 | B2 | 2/2014 | Bengtsson et al. |
| 9,200,313 | B2 | 12/2015 | Bengtsson et al. |
| 9,518,901 | B2 | 12/2016 | Hayashizaki et al. |
| 9,611,497 | B2 | 4/2017 | Pasloske et al. |
| 10,011,831 | B2 | 7/2018 | Pasloske et al. |
| 10,233,444 | B2 | 3/2019 | Pasloske et al. |
| 10,590,411 | B2 | 3/2020 | Pasloske et al. |
| 2003/0170617 | A1 | 9/2003 | Pasloske |
| 2010/0216194 | A1 | 8/2010 | Bengtsson et al. |
| 2011/0136180 | A1 | 6/2011 | Bengtsson et al. |
| 2012/0322112 | A1 | 12/2012 | Pasloske et al. |
| 2013/0143275 | A1 | 6/2013 | Pasloske et al. |
| 2013/0302783 | A1 | 11/2013 | Hayashizaki et al. |
| 2016/0168631 | A1 | 6/2016 | Bengtsson et al. |
| 2017/0218359 | A1 | 8/2017 | Pasloske et al. |
| 2018/0340175 | A1 | 11/2018 | Pasloske et al. |
| 2019/0270988 | A1 | 9/2019 | Pasloske et al. |

FOREIGN PATENT DOCUMENTS

| | | | |
|---|---|---|---|
| CN | 101386893 A | | 3/2009 |
| CN | 104928402 | | 9/2015 |
| CN | 104928402 A | * | 9/2015 |
| JP | 6-046900 | | 2/1994 |
| JP | 8-510004 | | 10/1996 |
| JP | 2017-209036 | | 11/2017 |
| JP | 2018-124 | | 1/2018 |
| WO | 94/026867 | | 11/1994 |
| WO | 2003/064605 | | 8/2003 |
| WO | 2008/135197 | | 11/2008 |
| WO | WO 2008/135196 A1 | * | 11/2008 |
| WO | WO 2008/135197 A1 | * | 11/2008 |
| WO | 2013/002354 | | 1/2013 |

OTHER PUBLICATIONS

Office Action issued Jul. 30, 2025, in corresponding Chinese Patent Application No. 202180031798.4, with English translation.
Dong Guanmu et al., PCR-based confirmation that infectious HIV-1 virions carry proviral DNA, 1994, vol. 9, No. 3, pp. 206-212, with English abstract.
Li Songbo et al., "Application of Polymerase Chain Reaction in the Field of Drug Quality Control", 2020, China Pharmacist, vol. 23 No. 1, pp. 130-133, with English abstract.
Extended European Search Report issued Jul. 3, 2024 in corresponding European Patent Application No. 21796238.0.
Chetverina, H. V. et al., "Simultaneous assay of DNA and RNA targets in the whole blood using novel isolation procedure and molecular colony amplification", Analytical Biochemistry, vol. 334, No. 2 (2004), pp. 376-381.

(Continued)

*Primary Examiner* — Jeffrey S Parkin
(74) *Attorney, Agent, or Firm* — Wenderoth, Lind & Ponack, L.L.P.

(57) ABSTRACT

Provided is a method for detecting an FNA virus in a biological sample, the method comprising: (1) a step for preparing a sample solution containing a biological sample, a protease, a nucleic acid that does not become a target of nucleic acid amplification, and at least one additive selected from the group consisting of chaotropic reagents and surfactants; (2) a step for preparing a nucleic acid amplification reaction solution containing the sample solution prepared in step (1) and containing a polypeptide having reverse transcriptase activity and DMA polymerase activity or a polypeptide having reverse transcription activity and a polypeptide having DNA polymerase activity; and (3) a step for amplifying a nucleic acid of the RNA virus in the reaction solution prepared in step (2).

4 Claims, No Drawings

Specification includes a Sequence Listing.

(56) References Cited

OTHER PUBLICATIONS

Greenfield, L. et al., "Chapter 6. Sample Preparation Methods" Diagnostic Molecular Microbiology: Principles and Applications, (May 1, 1997), pp. 122-137. XP002923321.
Zhong, J.F. et al., "Viral RNA extraction for in-the-field analysis", Journal of Virological Methods, vol. 144, No. 1-2 (2007), pp. 98-102.
Jothikumar, N. et al., "Development of an RNA extraction protocol for detection of waterborne viruses by reverse transcriptase quantitative PCR (RT-qPCR)", Journal of Virological Methods, vol. 169, No. 1 (2010), pp. 8-12.
Fan, Y. et al., "A rapid silica spin column-based method of RNA extraction from fruit trees for RT-PCR detection of viruses" Journal of Virological Methods, vol. 247 (2017), pp. 61-67.
Office Action issued May 13, 2025 in Japanese Patent Application No. 2022-518120, with English-language Translation.
Sung, H. et al., "Comparative Evaluation of Three Homogenization Methods for Isolating Middle East Respiratory Syndrome Coronavirus Nucleic Acids From Sputum Samples for Real-Time Reverse Transcription PCR", Ann Lab Med, 2016, vol. 36, No. 5, pp. 457-462.
International Search Report issued Jul. 20, 2021 in corresponding International (PCT) Patent Application No. PCT/JP2021/016998, with English language translation.
International Preliminary Report on Patentability issued Oct. 27, 2022 in corresponding International (PCT) Patent Application No. PCT/JP2021/016998, with English language translation.
Suzuki, Youichi et al., "Measuring Dengue Virus RNA in the Culture Supernatant of Infected Cells by Real-time Quantitative Polymerase Chain Reaction", Journal of Visualized Experiments, vol. 141, e58407, p. 1-12, 2018.
Second Office Action issued Mar. 26, 2026 in corresponding Chinese Patent Application No. 202180031798.4, with English language translation.
Office Action issued Mar. 16, 2026 in corresponding Korean Patent Application No. 10-2022-7040864, with English translation.
Decision of Rejection issued Jul. 13, 2026 in corresponding Chinese Patent Application No. 202180031798.4, with English translation.

* cited by examiner

RNA VIRUS DETECTION METHOD

TECHNICAL FIELD

The present invention relates to a method for detecting RNA virus contained in a biological sample, and a composition and a kit for the method.

BACKGROUND ART

It is important to detect a virus contained in a biological sample for clinical diagnosis and the like. For this purpose, a method comprising identifying the virus by amplifying a nucleic acid in a biological sample by PCR or the like and then detecting the amplified nucleic acid is performed. Since a biological sample contains various biological substances in addition to a nucleic acid, however, amplification inhibition or detection inhibition occurs when nucleic acid amplification is performed without purifying the nucleic acid from the biological sample. Thus, for detecting a target virus in a biological sample, for example, a method comprising purifying a nucleic acid from the biological sample using a column or the like and then subjecting the nucleic acid to a nucleic acid amplification reaction is adopted.

In addition, for suppressing amplification inhibition due to biological substances, a treating method of a nucleic acid-containing sample and a method comprising adding an additive to a nucleic acid amplification reaction solution have been reported. However, these method do not completely exclude the effect on the nucleic acid amplification reaction For example, a method comprising treating the RNA virus with a proteolytic enzyme arid then performing RT-Nested PCR to detect the RNA virus has been reported (see Patent Literature 1). Further, a method comprising treating a biological sample with a reducing agent or a polysaccharide-degrading enzyme in extraction of a virus nucleic acid and then subjecting the sample to RT-PCR to detect the virus has been reported (see Patent Literature 2).

CITATION LIST

Patent Literature

Patent Literature 1: JP-A H06-046900
Patent Literature 2: JP-A 2018-000124

SUMMARY OF INVENTION

Problems to be Solved by the Invention

A method comprising purifying a nucleic acid from, a biological sample using a nucleic acid binding carrier or the like and then subjecting the nucleic acid to a nucleic acid amplification reaction involves a risk of viral infection of a person performing the method until the virus is inactivated. Thus the sample needs to be handled at a containment level suitable for virus. That is, there are high cost and high risk problems. An object of the present invention is to provide a method for detecting an RNA virus in a biological sample with high sensitivity, with a reduced infection risk of a person performing the method, at a non-high-cost, and without complicated handling.

Solution to Problems

As a result of diligent studies to solve the above problems, the present inventors found that a target RNA virus nucleic acid can be efficiently amplified and detected with high sensitivity by a nucleic acid amplification reaction containing a polypeptide having reverse transcription activity and DNA polymerase activity, by going through a step of preparing a sample solution containing a biological sample, and at least one additive selected from the group consisting of a proteolytic enzyme, a nucleic acid that is not a target of nucleic acid amplification, a chaotropic reagent and a surfactant. Thus the present invention was completed.

The present invention relates to:

[1] A method for detecting an RNA virus in a biological sample, the method comprising:
 (1) a step of preparing a sample solution containing the biological sample and at least one additive selected from the group consisting of a proteolytic enzyme, a nucleic acid that is not a target of nucleic acid amplification, a chaotropic reagent and a surfactant,
 (2) a step of preparing a nucleic acid amplification reaction solution containing the sample solution prepared in step (1), and a polypeptide having reverse transcription activity and a polypeptide having DNA polymerase activity, or a polypeptide having reverse transcription activity and DNA polymerase activity, and
 (3) a step of amplifying a nucleic acid of the RNA virus in the reaction solution prepared in step (2);

[2] The method according to [1], wherein the proteolytic enzyme is proteinase K, thermolysin, or pronase;

[3] The method according to [1] or [2], wherein the chaotropic reagent, is guanidine or a salt thereof, urea, iodine or a salt thereof, or a combination thereof;

[4] The method according to any one of [1] to [3], wherein the biological sample is at least one selected from the group consisting of an oral scraping, pharyngeal swab, nasal swab, nasopharyngeal swab, nasal aspirate, sputum, bronchial lavage fluid, alveolar lavage fluid, rectal swab, saliva, blood, urine, and a stool suspension;

[5] The method according to any one of [1] to [4], wherein the RNA virus is at least one selected from the group consisting of influenza virus, RS virus, metapneumovirus, parainfluenza virus, SARS coronavirus, MERS coronavirus, measles virus, norovirus, rotavirus, sapovirus, and HIV;

[6] A method for preparing a sample solution for nucleic acid amplification, the method comprising a step of preparing a mixture containing a biological sample and at least one additive selected from the group consisting of a proteolytic enzyme, a nucleic acid that is not a target of the nucleic acid amplification, a chaotropic reagent, and a surfactant;

[7] A composition for the method for detecting an RNA virus in a biological sample according to any one of [1] to [5], comprising:
 (1) a sample solution containing at least one additive selected from the group consisting of a proteolytic enzyme, a nucleic acid that is not a target of nucleic acid amplification, a chaotropic reagent and a surfactant, and a biological sample, and
 (2) a polypeptide having reverse transcriptase activity and a polypeptide having DNA polymerase activity, or a polypeptide having reverse transcriptase activity and DMA polymerase activity;

[8] A kit for the method for detecting an RNA virus in a biological sample according to any one of [1] to [5], comprising:
 (1) at least one additive selected from the group consisting of a proteolytic enzyme, a nucleic acid that is not a target of nucleic acid amplification, a chaotropic reagent and a surfactant, and (2) a polypeptide having reverse transcriptase activity and a polypeptide having DMA polymerase activity, or a polypeptide having reverse transcriptase activity and DNA polymerase activity; etc.

Effects of the Invention

According to the present invention, a sample solution for nucleic acid amplification which has no risk, to a person who handles the sample solution and is suitable for nucleic acid amplification can be prepared by simple pretreatment of a biological sample which does not require special equipment and reagents such as organic solvents for nucleic acid extraction and purification and time for extraction and purification. A target nucleic acid can be detected by performing nucleic acid amplification using the sample solution. Therefore, according to the present invention, there is provided a method for detecting an RNA virus in a biological sample safely and simply with high sensitivity.

Embodiments to Carry Out the Invention

As used herein, "heat resistance" means resistance to heat treatment. For example, for enzymatically optimal temperature of 40 °C, maintaining the activity even at 50 °C or higher, 60 °C or higher or 70 °C or higher means improved "heat resistance". For example, in the case of Moloney murine leukemia virus-derived reverse transcriptase having an optimal temperature of 37 to 42 °C for the wild-type enzyme, reverse transcriptase mutants maintaining the enzyme activity at for example 43 °C or higher, preferably 45 °C or higher, more preferably 50 °C or higher are "heat resistant" or have "improved heat resistance".

Hereinafter, the present invention will be explained in detail.

1. Method for Detecting RNA Virus in Biological Sample of the Present Invention

The method for detecting an RNA virus in a biological sample of the present invention is characterized by comprising:

(1) a step of preparing a sample solution containing the biological sample, arid at least one additive selected from the group consisting of a proteolytic enzyme, a nucleic acid that is not a target of nucleic acid amplification, a chaotropic reagent and a surfactant, (2) a step of preparing a nucleic acid amplification reaction solution containing the sample solution prepared in step (1), and a polypeptide having reverse transcription activity and a polypeptide having DNA polymerase activity, or a polypeptide having reverse transcription activity and DNA polymerase activity, and (3) a step of amplifying a nucleic acid of the RNA virus in the reaction solution prepared in step (2).

[RNA Virus to be Detected]

The RNA virus to be detected by the method of the present invention is not limited as long as it has a genomic RNA. Examples of the RNA virus include a double-stranded RNA virus (dsRNA), a single-strand plus-strand RNA virus (+ strand type), and a single-strand minus-strand RNA virus (− strand type). Specific examples of the RNA virus include, but not particularly limited to, influenza virus, RS virus, metapneumovirus, parainfluenza virus, SARS coronavirus (including SARS-CoV-2; as used herein, SARS-CoV-2 is also referred to as 2019-nCoV), MERS coronavirus, measles virus, norovirus, rotavirus, sapovirus, and HIV.

[Biological Sample]

The biological sample as used herein is a sample suspected to contain an RNA virus, and includes a sample itself collected from a living body, and derivatives of the sample, for examples, a suspension, a solution or a dilution of the sample. Examples of the biological sample include, but not particularly limited to, an oral scraping, a pharyngeal swab, a nasal swab, a nasopharyngeal swab, a nasal aspirate, a sputum, a bronchial lavage fluid, an alveolar lavage fluid, a rectal swab, a saliva, blood, urine, and a stool suspension. In addition to the above-mentioned samples, examples of the biological sample include environment-derived samples suspected of containing an RNA virus, for example, environmental water (seawater, river water, lake water, sewage, household wastewater, industrial wastewater, etc.) and a suspension of a sample obtained by wiping with a swab or the like. Subject to be wiped include a floor, a wall, a work table, a sink, and various tools and apparatus, etc. of a manufacturing facility for food or the like, an experimental facility, a medical facility, a kitchen, a toilet, etc. The above-mentioned biological samples may be individually used in the present invention, or two or more biological samples may be mixed and then used in the present invention.

[Additive]

The additive used in the present invention is used for pretreatment of the biological sample. Examples of the additive include, but are not limited to, a proteolytic enzyme, a nucleic acid that is not a target for nucleic acid amplification, a chaotropic reagent, and a surfactant.

The proteolytic enzyme is not particularly limited as long as it can act on an envelope, a capsid, etc. of RNA virus, or a nuclease derived from a biological sample to release the genomic RNA existing in the capsid without degradation. Examples of the proteolytic enzyme include serine proteinase, acidic proteinase (aspartic acid proteinase, glutamic acid proteinase), alkaline proteinase, semi-alkaline proteinase, metal proteinase, cysteine proteinase, and N-terminal threonine proteinase. These enzymes may be used alone or in combination. The proteolytic enzyme may also be an endopeptidase. Examples of the endopeptidase include proteinase K as a representative of serine proteinase, and preferably thermolysin, pronase, and a mutant thereof. In the present invention, the concentration of the proteolytic enzyme used for pretreatment of the biological sample may be appropriately determined. For example, proteinase K or a mutant thereof can be used at a final concentration within a range of preferably 3 U/ml to 150 U/ml, more preferably 3 U/ml to 120 U/ml, and particularly preferably 30 U/ml to 100 U/ml. When combined with a chaotropic reagent or a surfactant, proteinase K or a mutant thereof may be used at a final concentration within a range of 1 U/ml to 120 U/ml, preferably 2 U/ml to 100 U/ml. As used herein, 1 U of proteinase K activity is defined as the amount of the enzyme that liberates folin-positive amino acids equivalent to 1.0 μmol of tyrosine in a reaction with denatured bovine hemoglobin as a substrate at 37 °C and pH 7.5 for a minute.

The nucleic acid that is not a target of nucleic acid amplification refers to a DNA and/or a RNA or a nucleic acid analog having a nucleotide sequence different from the RNA derived from the RNA virus that is the detection target of the present invention. As the nucleic acid that is not a target of nucleic acid amplification, various nucleic acids derived from viruses other than the RNA virus to be detected or organisms can be used. Examples of the nucleic acid that is not a target of nucleic acid amplification include, but not particularly limited to, a nucleic acid derived from *Escheri-*

*chia coli,* a nucleic acid derived from *Bacillus subtilis,* or a nucleic acid derived from yeast. Preferably, a ribosomal RNA derived from *Escherichia coli* or yeast is used.

The chaotropic reagent means a substance that reduces interaction between water molecules and thereby destabilizes molecular configuration present in a solution, Examples of the chaotropic reagent include, but not particularly limited to, guanidine and a salt thereof, urea, iodine and a salt thereof, and a combinations thereof. Examples of the guanidine salt include guanidine hydrochloride, guanidine nitrate, guanidine carbonate, and guanidine thiocyanate. Examples of iodide include lithium iodide, sodium iodide, potassium iodide, magnesium iodide, and calcium iodide. In the present invention, the chaotropic reagent can be used at a final concentration within a range of, for example, 0.5 w/V % to 5 w/V %, preferably 1 w/V % to 4 w/V %, and particularly preferably 2 w/V % to 4 w/V %. The chaotropic reagent can be used at a final molar concentration within a range of, for example, 40 μmol/ml to 450 μmol/ml, preferably 80 μmol/ml to 340 μmol/ml, and particularly preferably 160 μmol/ml to 340 μmol/ml.

Examples of the surfactant, that can be used in the present invention include, but not particularly limited to, an anionic surfactant (sodium dodecyl sulfate, sodium N-lauroyl sarcosine, sodium deoxycholate, etc.), a nonionic surfactant [Triton (registered trademark) X-100, Tween (registered trademark) 20, Nonidet (registered trademark) P-40, Brij (registered trademark) 35, etc.], and a cationic surfactant. For example, sodium dodecyl sulfate can be used at a final mass percent concentration (w/v%) within a range of, for example, 0.001 to 1%, preferably 0.005 to 1%, and more preferably 0.005 to 0.5%. The concentration is appropriately adjusted in combination with the proteolytic enzyme or an RT-qPCR reagent used.

[Polypeptides used for Nucleic Acid Amplification]

In the method of the present invention, a polypeptide having reverse transcription activity for synthesizing a cDNA from a genomic RNA of FNA virus, and a polypeptide having DNA-dependent DMA polymerase activity (herein, referred to as "DNA polymerase activity") for amplifying a DNA fragment derived from the cDNA can be used for a nucleic acid amplification reaction. The polypeptide having reverse transcription activity and the polypeptide having DNA polymerase activity may be separate polypeptides, or may be a single polypeptide having both activities. Examples of the polypeptide having reverse transcription activity include HIV reverse transcriptase, AMV reverse transcriptase, M-MLV reverse transcriptase, C therm. polymerase, and Tth polymerase, and further examples thereof include PrimeScript (trademark) RTase, Superscript (trademark) RTase, ReveRTra Ace (registered trademark) RTase, SMARTSeribe (trademark) RTase, Quantiscript RTase, and ProtoScript RTase.

Unless otherwise specified, the polypeptide having DNA polymerase activity as used herein is a DNA-dependent DNA polymerase. Preferable examples of the polymerase include a DNA polymerase belonging to family A (Pol I-type), a DNA polymerase belonging to family B (α-type), and a mixture of the above-mentioned two types of polymerases. Preferably, a heat-resistant DNA polymerase is used. Examples of the DNA polymerase include, but not particularly limited to, Taq DNA polymerase, Tth DNA polymerase, etc. derived from thermophilic eubacteria, and KOD DNA polymerase, Pfu DNA polymerase, etc. derived from thermophilic archaea. In a certain embodiment, it is preferable to use an α-type DNA polymerase (or a DNA polymerase belonging to family B) that has excellent accuracy. Examples of the α-type DNA polymerase include, but not; particularly limited to, commercially available polymerases, such as PrimeSTAR DNA polymerase (manufactured by TAKAPA BIO INC.), Tks Gflex DNA polymerase (manufactured by TAKARA BIO INC.), Pfu DNA polymerase, and KOD DNA polymerase (manufactured by TOYOBO CO., LTD.). Further, the polypeptide having DNA polymerase activity may be a single polypeptide having reverse transcription activity and DNA polymerase activity, and an example thereof is Tth polymerase.

The polypeptide having reverse transcription activity and the polypeptide having DNA polymerase activity, and the polypeptide having both activities may be in a native form or a mutant as long as they conform to the method of the present invention.

In the detection method of the present invention, the polypeptide having reverse transcription activity and the polypeptide having DNA polymerase activity, or the polypeptide having both activities may be a hot-start enzyme in combination with an antibody against the polypeptide for preventing non-specific amplification before reaction. Further, the polypeptide having reverse transcription activity and the polypeptide having DNA polymerase activity, or the polypeptide having both activities may be used in combination with an elongation factor such as PCNA, or various substances known to improve the efficiency of nucleic acid amplification reaction, for example, a surfactant, bovine serum albumin, an acidic high-molecular substance, an amphoteric amino acid, etc.

[Nucleic Acid Amplification Reaction Solution]

The nucleic acid amplification reaction solution used in the detection method of the present invention is a solution having a composition which comprises the sample solution containing the biological sample and the additive, and the polypeptide having reverse transcription activity and the polypeptide having DNA polymerase activity or the polypeptide having reverse transcription activity and DNA polymerase activity, and in which the polypeptide(s) can exert the activities. When nucleic acid amplification is carried out by RT-PCR, the reaction solution contains a buffer component for maintaining the optimal pH, a divalent metal salt (magnesium salt, manganese salt, etc.), and dNTP, and may further contain a neutral salt, a surfactant and other ingredients. The reaction solution may contain a primer pair for nucleic acid amplification of a specific region on the genomic RNA of an RNA virus to be detected, a nucleic acid probe for detection [for example, a quenching probe; Q probe), and a Taqman (registered trademark) probe] etc. Instead of the nucleic acid probe for detection, the reaction solution may contain an intercalator dye [for example, SYBR (registered trademark) Green, TB Green (registered trademark)] or the like. The reaction solution may further contain other reagents used for nucleic acid amplification reaction. For example, in the case of detecting 2019-nCoV, a primer pair and a nucleic acid probe for detection as described in the National Institute of Infectious Diseases Manual "Pathogen Detection Manual 2019-nCoV Ver. 2.9.1", a primer pair and a nucleic acid probe for detection as described in the Centers for Disease Control and Prevention (CDC) "2019-Novel Coronavirus (2019-nCoV) Real-time rRT-PCR Panel Primers and Probes" and the like can be preferably used. For the purpose of confirming reaction inhibition or the like, the nucleic acid amplification reaction may be multiplex detection in which an internal standard RNA having a different sequence from the nucleic acid derived from the RNA virus to be detected, a primer pair for detecting the internal standard RNA and a nucleic acid probe for the detection are used in combination. For example, in the case of detecting 2019-nCoV, N set primer, N set No. 2 primer/probe as described in the National Institute of Infectious Diseases manual, or N1 primer/probe, N2 primer/probe, or N3 primer/probe as described in the CDC manual can be preferably used.

Further, in the detection method of the present invention, two or more different gene regions on the genomic RNA of the virus to be detected can be amplified, and the different gene regions can be detected with two or more probes. In such a case, the two or more probes may be labeled with the same label. In other words, two regions may be detected at one wavelength. The labeled probes may be a combination of fluorescent labels based on FRET or non-FRET, or a combination of a fluorescent label and a quenching label. Examples of the fluorescent label include FAM, Cy5, ROX, and HEX. Examples of the quenching substance preferably include an eclipse called a dark quencher, and BHQ (registered trademark)-based labels.

In the case of detecting 2019-nCoV, for example, two or more selected from N1 primer/probe, N2 primer/probe, or N3 primer/probe as published by the CDC in "2019-Novel Coronavirus (2019-nCoV) Real-time rRT-PCR Panel Primers and Probes" can be used at. the same time to prepare the nucleic acid amplification reaction solution for simultaneously detecting two or more regions. The two or more probes contained in the reaction solution can be labeled with the same fluorescent dye, and thereby the virus can be detected with high sensitivity.

The nucleic acid amplification reaction solution is incubated under appropriate temperature conditions so that cDNA synthesis from the viral genome RNA target region and amplification of the cDNA occur in sequence. As the conditions, conditions for one-step RT-PCR well known to those skilled in the art can be adopted. The temperature, the time for keeping the temperature, and the number of cycles may be appropriately adjusted depending on the length of the target sequence, the primer, or the probe.

In the detection method of the present invention, (1) the sample solution containing a biological sample and at least one additive selected from the group consisting of a proteolytic enzyme, a nucleic acid that is not a target of nucleic acid amplification, a chaotropic reagent and a surfactant is prepared, and then added to the nucleic acid amplification reaction solution. Prior to addition to the nucleic acid amplification reaction solution, the sample solution may be kept warm or heated as described later.

In the detection method of the present invention, a biological sample can be subjected to a reverse transcription reaction and a nucleic acid amplification reaction without purifying a nucleic acid from an RNA virus in the biological sample. Thus, the amount of a template brought into the reverse transcription reaction and the nucleic acid amplification reaction is increased. For example, a biological sample treatment solution (the sample solution) can be brought into a reverse transcription reaction and a nucleic acid amplification reaction, for example, in an amount of 30 μl or less and 5 μl to 10 μl of a template solution per 50 μl of a reaction volume.

2. Method for Preparing Sample Solution for Nucleic Acid Amplification of the Present Invention The sample solution for nucleic acid amplification of the present invention is a mixture containing a biological sample, and at least one additive selected from the group consisting of a proteolytic enzyme, a nucleic acid that is not a target of nucleic acid amplification, a chaotropic reagent and a surfactant, as described in Section 1. Therefore, the method for preparing the sample solution for nucleic acid amplification of the present invention comprises a step of preparing a mixture containing the biological sample and the additive. The sample solution of the present invention may be prepared by mixing the biological sample and the additive, or may be prepared by directly suspending the biological sample in a solution containing the additive prepared in advance. The sample solution may contain two or more additives. The amount of each additive may be appropriately determined based on detection sensitivity of RNA virus, or the like.

The sample solution may be subjected to a nucleic acid amplification reaction after being held for a certain period of time, though the present invention is not particularly limited. Examples of the holding time include, bur. not limited to, 1 second to 30 minutes, preferably 10 seconds to 20 minutes, more preferably 20 seconds to 10 minutes, and further preferably 30 seconds to 5 minutes. Further, the sample solution may be held at two or more different temperatures. The sample solution containing a biological sample and at least one additive selected from the group consisting of a proteolytic enzyme, a nucleic acid that is not a target of nucleic acid amplification, a chaotropic reagent and a surfactant may be kept warm and/or heated before being added to the nucleic acid amplification reaction solution. For example, the sample solution can be kept warm and/or heated at room temperature or at a temperature in a range of 1 °C to 99 °C. When the sample solution contains a proteolytic: enzyme, the sample solution can be kept warm at for example 20 °C to 90 °C, preferably 30 °C to 80 °C, more preferably 40 °C to 70 °C, still more preferably 50 °C to 60 °C from the viewpoint of promoting the action of the enzyme, and may be kept warm for, for example, 1 second to 30 minutes, preferably 10 seconds to 20 minutes, more preferably 20 seconds to 10 minutes, and further preferably 30 seconds to 5 minutes. For example, the sample solution may be kept warm at 55 °C for 5 to 10 minutes. Further, the sample solution may be subjected to high temperature treatment in order to inactivate the proteolytic enzyme. Examples of temperature for the high temperature treatment include 91 °C to 99 °C, and preferably 93 °C to 97 °C. Examples of time for the high temperature treatment include 1 second to 10 minutes, and preferably 30 seconds to 5 minutes. The sample solution may be subjected to the high temperature treatment after the keep-warm treatment as described above, or may be subjected to only the high temperature treatment without the keep-warm treatment. Thus, the method for preparing the sample solution for nucleic acid amplification of the present invention may further comprise a step of holding the mixture containing the biological sample and the additive for a certain period of time. In another aspect, the method for preparing the sample solution for nucleic acid amplification of the present invention may further comprise a step of keeping warm and/or heating the mixture containing the biological sample and the additive.

3. Composition for Detecting RNA Virus in Biological Sample of the Present Invention The composition of the present invention is a composition used as the nucleic acid amplification reaction solution used for the method for detecting RNA virus of the present invention, and characterized by comprising the sample solution containing a biological sample and at least one additive selected from the group consisting of a proteolytic enzyme, a nucleic acid that is not a target of nucleic acid amplification, a chaotropic reagent and a surfactant, and the polypeptide having reverse transcriptase activity and the polypeptide having DNA polymerase activity or the polypeptide having reverse transcriptase activity and DNA polymerase activity, as described in Section 1. When the sample solution contains a proteolytic enzyme, the proteolytic enzyme is preferably an inactivated proteolytic enzyme that is inactivated after preparation of the sample solution as described in Section 2 so that the polypeptide having DNA polymerase activity in the composition of the present invention is not degraded. The composition of the present invention may further comprise various components necessary for the polypeptide having reverse transcriptase activity and the polypeptide having DNA polymerase activity or the polypeptide having reverse transcriptase activity and DNA polymerase activity to exert the activities. Furthermore, the composition may comprise a primer pair for nucleic acid amplification of a specific region on the genomic RNA of the target RNA virus, a nucleic acid probe for detection, and the like. Examples of a nucleic acid detection method using the nucleic acid probe include methods comprising use of a TaqMan (registered trademark) probe, a Q probe, a Molecular Beacon, and the like. In the above-mentioned methods, for example, the target nucleic acid can be detected by monitoring the degradation of the nucleic acid probe or by hybridizing the nucleic acid probe to the nucleic acid and performing a melting curve analysis. Other conditions for the detection step may be appropriately determined in consideration of the type and sequence of a nucleic acid to be detected, the type of probes, and the like. The composition of the present invention may comprise, instead of the detection nucleic acid probe, an intercalator dye [for example, SYBR (registered trademark) Green, TB Green (registered trademark)] or the like. For example, in the case of detecting 2019-nCoV coronavirus, a primer pair and a nucleic acid probe for detection as described in the National Institute of Infectious Diseases Manual, a primer pair and a nucleic acid probe for detection as described in the US CDC Manual, or the like can be preferably used. In addition, the composition of the present invention may comprise a primer pair for internal standard amplification and a nucleic acid probe for the detection for the purpose of confirming reaction inhibition.

4. Kit for Method of Detecting RNA Virus in Biological Sample of the Present Invention The kit of the present invention is characterized by comprising:

(1) at least one additive selected from the group consisting of a proteolytic enzyme, a nucleic acid that is not a target of nucleic acid amplification, a chaotropic reagent and a surfactant, and (2) a polypeptide having reverse transcriptase activity and a polypeptide having DNA polymerase activity, or a polypeptide having reverse transcriptase activity and DNA polymerase activity, as described in Section 1.

The kit of the present invention may comprise each element as described above in a suitable form for performing “the method for detecting an RNA virus in a biological sample of the present invention” and preparing “the composition for detecting an RNA virus in a biological sample of the present invention”. Thus, the kit of the present invention may further comprise a diluent for preparing the sample solution for nucleic acid amplification, a buffer for preparing the nucleic acid amplification reaction solution for detecting RNA virus, and the like. The kit of the present invention may comprise a reagent for detecting an RNA virus by the method of the present invention. Examples of the reagent include, but not limited to, a buffer component, a divalent metal, salt, dNTP, and a neutral salt. As one aspect of the present invention, provided is a kit comprising a premix reaction solution containing the polypeptide having reverse transcriptase activity and the polypeptide having DNA polymerase activity, or the polypeptide having reverse transcriptase activity and DNA polymerase activity, and various components necessary for the polypeptide(s) to exert the activities at appropriate concentrations; and the additive (s).

The kit of the present invention may further comprise a primer pair for nucleic acid amplification of a specific region on the genomic RNA of the target RNA virus, a nucleic acid probe for detection, and the like. Instead of the nucleic acid probe for detection, the kit of the present invention may comprise an intercalator dye or the like. For example, in the case of detecting 2019-nCoV coronavirus, a primer pair and a nucleic acid probe for detection as described in the National Institute of Infectious Diseases Manual, a primer pair and a nucleic acid probe for detection as described in the US CDC Manual, or the like can be preferably used. In addition, the kit of the present invention may comprise a primer pair for internal standard amplification arid a nucleic acid probe for the detection for the purpose of confirming reaction inhibition.

Hereinafter, the present invention will be more specifically explained with reference to Examples, which the scope of the present invention is not limited to.

EXAMPLE 1

Experiment for Additives—1

The detection method of the present invention was demonstrated. First, an RNA positive control having the nucleotide sequence shown in SEQ ID NO: 4, called “N2 set”, which is one of RNA positive controls used for sensitivity tests of primer pairs and nucleic acid probes for detection as described in the National Institute of Infectious Diseases Manual “Pathogen Detection Manual 2019-nCoV Ver. 2.9.1”, was prepared by a conventional method. Next, a commercially available sputum sample (manufactured by NOVA Biologics) was diluted 3-fold with physiological saline to prepare a stock suspension of the sputum sample. The stock suspension was further diluted 20-fold with physiological saline, and then mixed with the RNA positive control to prepare a biological sample suspension. A mixture that did not contain the sputum sample was also prepared. Then, Proteinase K (manufactured by TAKARA BIO INC., about 400 U/ml) as a proteolytic enzyme, guanidine thiocyanate (CAS registration number 593-84-0) (manufactured by TOKYO CHEMICAL INDUSTRY CO., LTD.) as a chaotropic reagent, or sodium dodecyl sulfate (manufactured by TOKYO CHEMICAL INDUSTRY CO., LTD.) as a surfactant was used as the additive to be mixed with the biological sample. In addition, a control was prepared by adding nothing to the biological sample suspension.

To the biological sample suspension, a final concentration of 3.5 U/ml (175 μg/ml), 7 U/ml (350 μg/ml), 35 U/ml (1750 μg/ml) or 70 U/ml (3500 μg/ml) of Proteinase K, a final concentration of 209 μmol/ml of guanidine thiocyanate, and a final concentration of 0.01% (w/v) of sodium dodecyl sulfate were added; and kept warm at 55 °C for 5 to 10 minutes and then heated at 95 °C for 5 minutes, or directly heated at 95 °C for 5 minutes without keep warm. To a mixture thus obtained, the RNA positive control was added so as to become 2.5×10^5 copies/reaction, and then subjected to RT-PCR. As RT-PCR reagents. One Step PrimeScript (trademark) III RT-qPCR Mix (manufactured by TAKARA BIO INC.) was used. Specifically, 5 μl of a mixture as obtained above was mixed with 25 μl of 2×RT-qPCR Mix; NIID_2019-nCoV_N_F primer (final concentration: 0.5 μM) and NIID_2019-nCoV_N_R primer (final concentration: 0.7 μM) described in the National Institute of Infectious Diseases Manual, having the nucleotide sequences of SEQ ID NOs: 1 and 2; NIID_2019-nCoV_N_P probe (final concentration: 0.2 μM, 5' FAM labeled, 3' BHQ1 labeled) having the nucleotide sequence of SEQ ID NO: 3; and RNase Free $H_2O$ to prepare a reaction mixture having a final volume of 50 μl.

As a thermal cycler, Thermal Cycler Dice (registered trademark) Real Time System III (Cy5) with PC (manufactured by TAKARA BIO INC.) was used. PCR was performed under conditions of 52 °C for 5 minutes and 95 °C for 10 seconds, followed by 45 cycles of 95 °C for 5 seconds and 60 °C for 30 seconds. Results are shown in Table 1.

TABLE 1

| Sputum suspension supernatant | Additive | | | Keep warm/heat treatment | | Ct value RNA positive control |
|---|---|---|---|---|---|---|
| | ProK | SDS | GT | 55 °C | 95 °C/ 5 min | |
| None (PBP) | — | — | — | — | — | 23.6 |
| ○ | 3.5 U/ml | — | — | — | ○ | 28.8 |
| ○ | 3.5 U/ml | — | — | ○/5 min | ○ | 28.2 |
| ○ | 3.5 U/ml | — | — | ○/10 min | ○ | 28.7 |
| ○ | 7.0 U/ml | — | — | — | ○ | 26.9 |
| ○ | 7.0 U/ml | — | — | ○/5 min | ○ | 26.4 |
| ○ | 7.0 U/ml | — | — | ○/10 min | ○ | 26.7 |
| ○ | 35 U/ml | — | — | — | ○ | 28.6 |
| ○ | 35 U/ml | — | — | ○/5 min | ○ | 26.9 |
| ○ | 35 U/ml | — | — | ○/10 min | ○ | 26.5 |
| ○ | 70 U/ml | — | — | — | ○ | 26.7 |
| ○ | 70 U/ml | — | — | ○/5 min | ○ | 25.3 |
| ○ | 70 U/ml | — | — | ○/10 min | ○ | 24.8 |
| ○ | 3.5 U/ml | 0.01% | — | — | ○ | 24.0 |
| ○ | 3.5 U/ml | 0.01% | — | ○/5 min | ○ | 23.9 |
| ○ | 3.5 U/ml | 0.01% | — | ○/10 min | ○ | 23.8 |
| ○ | 3.5 U/ml | — | 2.5% | — | ○ | 23.9 |
| ○ | 3.5 U/ml | — | 2.5% | ○/5 min | ○ | 23.9 |
| ○ | 3.5 U/ml | — | 2.5% | ○/10 min | ○ | 23.9 |

As seen from Table 1, when a high concentration 35 to 70 U/ml (175 μg/ml to 3500 μg/ml) of Proteinase K ("ProK" in the table) was added, a Ct value was almost the same as that when the biological sample suspension was not added, and thus the influence of the biological sample suspension was eliminated. When a combination of 3.5 U/ml of Proteinase K and guanidine thiocyanate ("GT" in the table) or a combination of 3.5 U/ml of Proteinase K and 0.01% of sodium dodecyl sulfate ("SDS" in the table) was added, a Ct value was almost the same as that when the biological sample suspension was not added, and thus the influence of the biological sample suspension was eliminated. Therefore, it was found that a high concentration of Proteinase K or a combination of Proteinase K with guanidine thiocyanate and/or sodium dodecyl sulfate is effective as the additive of the present invention. Even when the keep warm treatment of the sample solution at 55 °C was omitted, it was possible to detect the RNA virus in the sample.

EXAMPLE 2

Experiment for Additives—2

The detection method of the present invention was demonstrated by using an inactivated virus. In this Example, NATtrol (trademark) Influenza A/B Positive Control (manufactured by ZeptoMetrix) was used as the inactivated RNA virus. The inactivated RNA virus being undiluted was mixed with, or the inactivated RNA virus was diluted 10 to 20-fold with physiological saline and then mixed with the sputum sample prepared in Example 1 to prepare a biological sample suspension. A mixture that did not contain the sputum sample was also prepared.

Proteinase K as a proteolytic enzyme, guanidine thiocyanate as a chaotropic reagent, or sodium dodecyl sulfate as a surfactant was used as the additive.

The experiment was carried out as follows. Specifically, to the biological sample suspension, a final concentration of 3.5 U/ml or 70 U/ml of Proteinase K, a final concentration of 2.5% (w/v) of guanidine thiocyanate, or a final concentration of 0.01% (w/v) of sodium dodecyl sulfate was added in combination. A mixture was kept warm at room temperature or 55 °C for 5 minutes, heated at 95 °C for 5 minutes, and then subjected to evaluation by RT-qPCR. As RT-PCR reagents. One Step PrimeScript (trademark) III RT-qPCR Mix (manufactured by TAKARA BIO INC.) was used. Specifically, 5 μl of the biological sample suspension containing the additive(s) was mixed with 25 μl of 2×RT-qPCR Mix, IAmg-F01 and IAmg-R01 primers (final concentration: 0.2 μM) having the nucleotide sequences of SEQ ID NOs: 5 and 6, IAmg-PR01 probe for influenza virus A detection (final concentration: 0.2 μM, 5' FAM labeled, 3' BHQ1 labeled) having the nucleotide sequence of SEQ ID NO: 7, and RNase Free $H_2O$ to prepare a reaction mixture having a final volume of 50 μl.

As a thermal cycler, Thermal Cycler Dice (registered trademark) Real Time System III (Cy5) with PC (manufactured by TAKARA BIO INC.) was used. PCR was performed under conditions of 52 °C for 5 minutes and 95 °C for 10 seconds, followed by 45 cycles of 95 °C for 5 seconds and 60 °C for 30 seconds. Amplification results were evaluated by comparing Ct values with a Ct value of a control to which no additive was added. Results are shown in Table 2.

TABLE 2

| | | | | | |
|---|---|---|---|---|---|
| | | ProK | 70 U/ml | 3.5 U/ml | 3.5 U/ml |
| | | SDS | — | ○ | — |
| | | GT | — | — | ○ |
| | | Keep warm/heat treatment | 55 °C/5 min 95 °C/5 min | — 95 °C/5 min | — 95 °C/5 min |
| Biological sample suspension | Stock suspension | 10-fold diluted inactivated virus | 32.6 | 36.2 | 32.5 |
| | | Undiluted inactivated virus | 29.9 | 32.3 | 29.4 |
| | (1/10) | 10-fold diluted inactivated virus | 32.6 | 32.7 | 32.4 |
| | | Undiluted inactivated virus | 29.4 | 29.0 | 28.8 |
| | (1/20) | 10-fold diluted inactivated virus | 32.8 | 32.4 | 32.5 |
| | | Undiluted inactivated virus | 29.6 | 28.9 | 28.8 |
| | None (PBS) | 10-fold diluted inactivated virus | 33.2 | 32.2 | 32.3 |
| | | Undiluted inactivated virus | 29.2 | 28.8 | 28.9 |

As seen from Table 2, when high concentration 70 U/ml of Proteinase K ("ProK" in the table) was added to the stock suspension to 20-fold dilution of the biological sample, a Ct value was the same as that when the biological sample suspension was not added, and thus the influence of the biological sample suspension was eliminated. When a combination of 3.5 U/ml of Proteinase K and guanidine thiocyanate ("GT" in the table) was added, a Ct value was the same as that when high concentration 70 U/ml of Proteinase K was added. Further, when a combination of 3.5 U/ml of Proteinase K and 0.01% of sodium dodecyl sulfate ("SDS" in the table) was added to a 10- to 20-fold dilution of the biological sample suspension, a Ct value was the same as that when high concentration 70 U/ml of Proteinase K was added. Therefore, it was found that a high concentration of Proteinase K or a combination of Proteinase K with guanidine thiocyanate and/or sodium dodecyl sulfate is effective as the additive of the present invention even when detecting an RNA from a biological sample spiked with an inactivated virus, which is close to an actual sample.

EXAMPLE 3

Experiment for Biological Samples

The detection method of the present invention was demonstrated by using an inactivated virus. As the inactivated RNA virus, a commercially available inactivated RNA virus, NATtrol (trademark) SARS_CORONA Positive Control (manufactured by ZeptoMetrix) was used, and diluted 1.2-fold and 12-fold with physiological saline. As the biological sample, a commercially available saliva (manufactured by LEE BIOSOLUTIONS) was used with being undiluted or diluted with a virus transport medium (product name: virus transport medium (VTM), manufactured by Sugiyama-gen). The biological sample was mixed with the inactivated virus dilution to prepare a biological sample suspension. As the additive to be mixed with the biological sample suspension. Proteinase K as a proteolytic enzyme was used.

The experiment was carried out as follows. Specifically, a final concentration of 70 U/ml or 17.5 U/ml of Proteinase K was added to the biological sample suspension. A mixture was left at room temperature for 5 minutes, held at 55 °C for 5 minutes, heated at 95 °C for 5 minutes, and then subjected to evaluation by RT-qPCR. The same RT-qPCR reagents as used in Example 1 were used. Specifically, 10 µl of the biological sample suspension containing the additive was mixed with 2×RT-qPCR Mix, PCR forward Primer N1_SARS_COV_F and R primers (final concentration: 0.2 µM) having the nucleotide sequences of SEQ ID NOs: 8 and 9, PCR Forward Primer N2_SARS COV_F and R primers (final concentration: 0.2 µM) having the nucleotide sequences of SEQ ID NOs: 11 and 12, N1_SARS COV_P probe for SARS_CORONA detection (final concentration: 0.2 µM, 5' Cy5 labeled, 3' BHQ3 labeled) having the nucleotide sequence of SEQ ID NO: 10, N2_SARS COV_P probe for SARS_CORONA detection (final concentration: 0.2 µM, 5' Cy5 labeled, 3' BHQ3 labeled) having the nucleotide sequence of SEQ ID NO: 13, and RNase Free $H_2O$ to prepare a reaction mixture having a final volume of 50 µl.

A thermal cycler and PCR conditions were the same as Example 1. Amplification results were evaluated by comparing Ct values with a Ct value of a control to which no additive was added. Results are shown in Table 3.

TABLE 3

| Biological sample | Natrol added amount | Treatment with ProteinaseK: Biological sample added amount | Treatment with ProteinaseK: ProK added amount (unit conc.) | Copies/ reaction | RT-PCR reaction Ct value |
|---|---|---|---|---|---|
| Saliva | 1 μl | 39 μl | 10 μl | 500 | 35.4 |
| | | | (70 U/ml) | 50 | 38.2 |
| | | | 10 μl | 500 | 35.9 |
| | | | (17.5 U/ml) | 50 | 38.8 |
| Saliva + | | 19 μl | 10 μl | 500 | 35.3 |
| VTM | | (saliva) + | (70.0 U/ml) | 50 | 38.4 |
| | | 20 μl | 10 μl | 500 | 35.3 |
| | | (VTM) | (17.5 U/ml) | 50 | 39.1 |

As seen from Table 3, nucleic acid amplification was observed in all the biological sample suspensions obtained by adding the inactivated virus to the undiluted saliva or the mixture of saliva and VTM. Both when 70 U/ml of Proteinase K ("ProK" in the table) was added as the additive and when 17.5 U/ml of Proteinase K was added as the additive, the same Ct value was obtained. Therefore, it was found that the present invention is effective even when detecting an RNA from a biological sample such as saliva spiked with an inactivated virus.

EXAMPLE 4

Experiment for Uracil-N-Glucosidase (UNG) Treatment

The detection method of the present invention was demonstrated by using the same biological sample suspension and the same additive as Example 3.

In this Example, treatment of the biological sample suspension before RT-PCR was performed in the same way as in Example 3. Evaluation by RT-qPCR was also performed in the same way as in Example 3 except that one Step PrimeScript (trademark) III RT-qPCR Mix, with UNG (manufactured by TAKARA BIO INC.) was used as RT-PCR reagents instead of One Step FrimeScript (trademark) III RT-qPCR Mix (manufactured by TAKARA BIO INC.). A thermal cycler and PCR conditions were the same as Example 1. Amplification results were evaluated by comparing Ct values with a Ct value of a control to which no additive was added. Results are shown in Table 4.

TABLE 4

| Bioligical sample | Treatment with ProteinaseK: Biological sample (Added amount) | Treatment with ProteinaseK: ProK (Final conc.) | Treatment with ProteinaseK: Natrol (Added amount) | Inactivated virus in RT-PCR reaction: Copies/ reaction | Inactivated virus in RT-PCR reaction: Ct value |
|---|---|---|---|---|---|
| Saliva | 39 μl | 10 μl | 1 μl | 500 | 36.1 |
| | | (70 U/ml) | | 50 | 39.1 |
| | | 10 μl | | 500 | 36.5 |
| | | (17.5 U/ml) | | 50 | 38.7 |
| Saliva + | 19 μl | 10 μl | | 500 | 36.5 |
| VTM | (saliva) + | (70 U/ml) | | 50 | 39.0 |
| | 20 μl | 10 μl | | 500 | 36.0 |
| | (VTM) | (17.5 U/ml) | | 50 | 39.0 |

As seen from Table 4, nucleic acid amplification was observed in ail the biological sample suspensions obtained by adding the inactivated virus to the undiluted saliva or the mixture of saliva and VTM. Both when 70 U/ml of Proteinase K ("ProK" in the table) was added as the additive and when 17.5 U/ml of Proteinase K was added as the additive, the same Ct value was obtained. Therefore, it was found that the present invention is effective even in RT-qPCR containing uracil-N-glucosidase and dUTP for preventing contamination by amplified products.

INDUSTRIAL APPLICABILITY

A nucleic acid derived from an RNA virus contained in a sample can be detected without requiring isolation of the nucleic acid by using the detection method of the present invention. Thus the present invention greatly contributes to the field of clinical diagnosis.

SEQUENCE LISTING FREE TEXT

SEQ ID NO: 1: PCR Forward Primer NIID_2019-nCOV_N_F2

SEQ ID NO: 2: PCR Reverse Primer NIID_2019-nCOV_N_R2

SEQ ID NO: 3: Probe NIID_2019-nCOV_N_P2. 5'-end is labeled FAM and 3'-end is labeled BHQ1

SEQ ID NO: 4: RNA positive control sequence for 2019-nCoV N2 set

SEQ ID NO: 5: PCR Forward Primer IAmg-F01

SEQ ID NO: 6: PCR Reverse Primer IAmg-R01

SEQ ID NO: 7: Probe IAmg-PB1, 5'-end is labeled FAM and 3'-end is labeled BHQ1

SEQ ID NO: 8 PCR Forward Primer N1_SARS COV_F

SEQ ID NO: 9 PCR Reverse Primer N1_SARS_COV_R

SEQ ID NO: 10 N1_SARS COV_P. 5'-end is labeled Cy5 and 3'-end is labeled BHQ3

SEQ ID NO: 11 PCR Forward Primer N2_SARS COVF

SEQ ID NO: 12 PCR Reverse Primer N2.SARS GOVJR

SEQ ID NO: 13 N2_SARS COV_p. 5'-end is labeled Cy5 and 3'-end is labeled BHQ3

The invention claimed is:

1. A method for detecting an RNA virus in a biological sample, the method comprising:

(1) obtaining or preparing a biological sample suspected of containing an RNA virus, (2) adding 35 U/ml to 70 U/ml of proteinase K to the biological sample and incubating at room temperature for 30 minutes or less, (3) subjecting the biological sample to a high temperature treatment at 91 °C to 99 °C for 30 seconds to 5 minutes to inactivate the proteinase K, (4) adding the biological sample to a nucleic acid amplification reaction mixture containing a polypeptide having reverse transcription activity and a polypeptide having DNA polymerase activity, or a polypeptide having reverse transcription activity and DNA polymerase activity, and primers and probes specific to the RNA virus, and (5) performing reverse transcription and nucleic acid amplification on the biological sample and detecting any viral amplified products in the biological sample.

2. The method according to claim 1, wherein the biological sample further contains guanidine or a salt thereof.

3. The method according to claim 1, wherein the biological sample is at least one selected from the group consisting of an oral scraping, pharyngeal swab, nasal swab, nasopharyngeal swab, nasal aspirate, sputum, bronchial lavage fluid, alveolar lavage fluid, rectal swab, saliva, blood, urine, and a stool suspension.

4. The method according to claim 1, wherein the RNA virus is at least one selected from the group consisting of influenza virus, RS virus, metapneumovirus, parainfluenza virus, SARS coronavirus, MERS coronavirus, measles virus, norovirus, rotavirus, sapovirus, and HIV.

* * * * *

SEQUENCE LISTING

```
<160> NUMBER OF SEQ ID NOS: 13

<210> SEQ ID NO 1
<211> LENGTH: 20
```

<212> TYPE: DNA
<213> ORGANISM: Artificial Sequence
<220> FEATURE:
<223> OTHER INFORMATION: PCR Forward Primer NIID_2019-nCOV_N_F2

<400> SEQUENCE: 1
aaattttggg gaccaggaac 20

<210> SEQ ID NO 2
<211> LENGTH: 20
<212> TYPE: DNA
<213> ORGANISM: Artificial Sequence
<220> FEATURE:
<223> OTHER INFORMATION: PCR Reverse Primer NIID_2019-nCOV_N_R2

<400> SEQUENCE: 2
tggcagctgt gtaggtcaac 20

<210> SEQ ID NO 3
<211> LENGTH: 20
<212> TYPE: DNA
<213> ORGANISM: Artificial Sequence
<220> FEATURE:
<223> OTHER INFORMATION: Probe NIID_2019-nCOV_N_P2. 5'-end is labeled
FAM and 3'-end is labeled BHQ1

<400> SEQUENCE: 3
atgtcgcgca ttggcatgga 20

<210> SEQ ID NO 4
<211> LENGTH: 337
<212> TYPE: RNA
<213> ORGANISM: Artificial Sequence
<220> FEATURE:
<223> OTHER INFORMATION: RNA positive control sequence for 2019-nCoV N2
set

<400> SEQUENCE: 4
gggcagacgu gguccagaac aaacccaagg aaauuuuggg gaccaggaac uaaucagacg 60
gauccagcua gcgcauugga ucucgcaaau ugcacaauuu gcccccagcg cuucagcguu 120
cuucggaaug ucgcgcauug gcauggaagu cacaccuucg ggaacguggu ugaccuacac 180
agcugccauc aaauuggaug acaaagaucc aaauuucaaa gaucaaguca uuuugcugaa 240
uaagcauauu gacgcauaca aaacauuccc accaacagag ccuaaaaagg acaaaaagaa 300
gaaggcugau gaaacucaag ccuuaccgca gagacag 337

<210> SEQ ID NO 5
<211> LENGTH: 29
<212> TYPE: DNA
<213> ORGANISM: Artificial Sequence
<220> FEATURE:
<223> OTHER INFORMATION: PCR Forward Primer IAmg-F01

<400> SEQUENCE: 5
ccmaggtcga aacgtaygtt ctctctatc 29

<210> SEQ ID NO 6
<211> LENGTH: 32
<212> TYPE: DNA
<213> ORGANISM: Artificial Sequence
<220> FEATURE:
<223> OTHER INFORMATION: PCR Reverse Primer IAmg-R01

<400> SEQUENCE: 6

```
tgacagraty ggtcttgtct ttagccaytc ca                                   32


<210> SEQ ID NO 7
<211> LENGTH: 22
<212> TYPE: DNA
<213> ORGANISM: Artificial Sequence
<220> FEATURE:
<223> OTHER INFORMATION: Probe IAmg-PB1. 5'-end is labeled FAM and
      3'-end is labeled BHQ1

<400> SEQUENCE: 7

atytcggctt tgagggggcc tg                                              22


<210> SEQ ID NO 8
<211> LENGTH: 23
<212> TYPE: DNA
<213> ORGANISM: Artificial Sequence
<220> FEATURE:
<223> OTHER INFORMATION: PCR Forward Primer N1_SARS COV_F

<400> SEQUENCE: 8

gaccccaatc aaaccaacgt agt                                             23


<210> SEQ ID NO 9
<211> LENGTH: 24
<212> TYPE: DNA
<213> ORGANISM: Artificial Sequence
<220> FEATURE:
<223> OTHER INFORMATION: PCR Reverse Primer N1_SARS COV_R

<400> SEQUENCE: 9

tctggttatt gtcagttgaa tctg                                            24


<210> SEQ ID NO 10
<211> LENGTH: 24
<212> TYPE: DNA
<213> ORGANISM: Artificial Sequence
<220> FEATURE:
<223> OTHER INFORMATION: N1_SARS COV_P. 5'-end is labeled Cy5 and 3'-end
      is labeled BHQ3

<400> SEQUENCE: 10

cccccgcatt acatttggtg gacc                                            24


<210> SEQ ID NO 11
<211> LENGTH: 20
<212> TYPE: DNA
<213> ORGANISM: Artificial Sequence
<220> FEATURE:
<223> OTHER INFORMATION: PCR Forward Primer N2_SARS COV_F

<400> SEQUENCE: 11

ttacaaacat tggccgcaaa                                                 20


<210> SEQ ID NO 12
<211> LENGTH: 18
<212> TYPE: DNA
<213> ORGANISM: Artificial Sequence
<220> FEATURE:
<223> OTHER INFORMATION: PCR Reverse Primer N2_SARS COV_R

<400> SEQUENCE: 12

gcgtgacatt ccaaagaa                                                   18


<210> SEQ ID NO 13
<211> LENGTH: 23
```

-continued

```
<212> TYPE: DNA
<213> ORGANISM: Artificial Sequence
<220> FEATURE:
<223> OTHER INFORMATION: N2_SARS COV_P. 5'-end is labeled Cy5 and 3'-end
      is labeled BHQ3

<400> SEQUENCE: 13

acaatttgct ccaagtgcct ctg                                              23
```